US008329976B2

(12) United States Patent
Freiding et al.

(10) Patent No.: US 8,329,976 B2
(45) Date of Patent: Dec. 11, 2012

(54) METHOD FOR MANUFACTURING A NET PATTERNED ADHESIVE LAYER

(75) Inventors: Markus Freiding, Helsingborg (SE); Peter Kwok Hing Lam, Frederiksberg (DK)

(73) Assignee: Coloplast A/S, Humlebaek (DK)

( * ) Notice: Subject to any disclaimer, the term of this patent is extended or adjusted under 35 U.S.C. 154(b) by 356 days.

(21) Appl. No.: 12/451,824

(22) PCT Filed: Jun. 4, 2008

(86) PCT No.: PCT/EP2008/056909
§ 371 (c)(1),
(2), (4) Date: Feb. 26, 2010

(87) PCT Pub. No.: WO2008/148797
PCT Pub. Date: Dec. 11, 2008

(65) Prior Publication Data
US 2010/0168635 A1 Jul. 1, 2010

(30) Foreign Application Priority Data

Jun. 4, 2007 (DK) ................................. 2007 00811

(51) Int. Cl.
*A61F 13/00* (2006.01)
(52) U.S. Cl. ................ 602/55; 602/41; 602/42; 602/43; 602/54
(58) Field of Classification Search ............... 602/41–59
See application file for complete search history.

(56) References Cited

U.S. PATENT DOCUMENTS

| 5,540,922 | A | 7/1996 | Fabo |
| 5,782,787 | A * | 7/1998 | Webster .......................... 602/46 |
| 6,123,958 | A | 9/2000 | Cheong et al. |
| 6,171,648 | B1 | 1/2001 | Himmelsbach et al. |
| 6,537,658 | B1 | 3/2003 | Bruss et al. |
| 2003/0153860 | A1* | 8/2003 | Nielsen et al. .................. 602/43 |
| 2004/0127830 | A1 | 7/2004 | Sigurjonsson et al. |
| 2005/0228329 | A1 | 10/2005 | Boehringer et al. |
| 2010/0168633 | A1* | 7/2010 | Bougherara et al. ............ 602/43 |

FOREIGN PATENT DOCUMENTS

| DE | 29 00 319 A1 | 10/1979 |
| EP | 0 437 916 A2 | 7/1991 |
| EP | 0 532 275 A1 | 3/1993 |
| EP | 0 633 758 | 1/1995 |
| EP | 1 093 780 A2 | 4/2001 |
| GB | 2 019 807 A | 11/1979 |
| GB | 2 425 487 A | 11/2006 |
| WO | WO 93/19710 | 10/1993 |
| WO | WO 2005/028581 A1 | 3/2005 |

* cited by examiner

*Primary Examiner* — Kim M Lewis
(74) *Attorney, Agent, or Firm* — Jacobson Holman PLLC

(57) ABSTRACT

A method for making a net patterned adhesive layer by a mold, and a wound dressing having a net patterned adhesive layer.

14 Claims, 5 Drawing Sheets

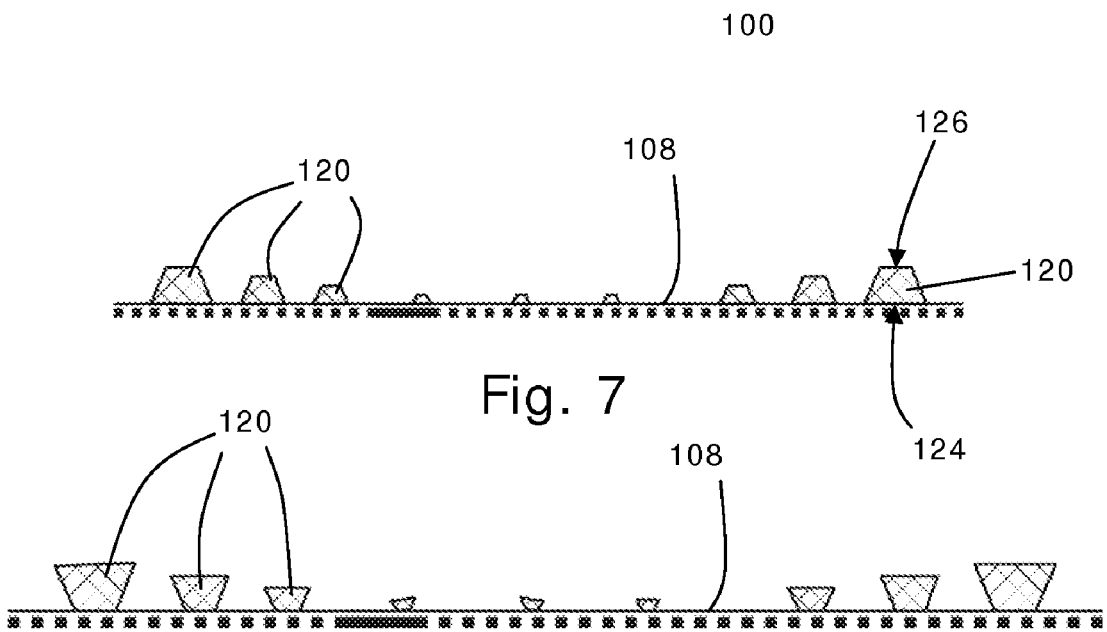
Fig. 7
Fig. 8
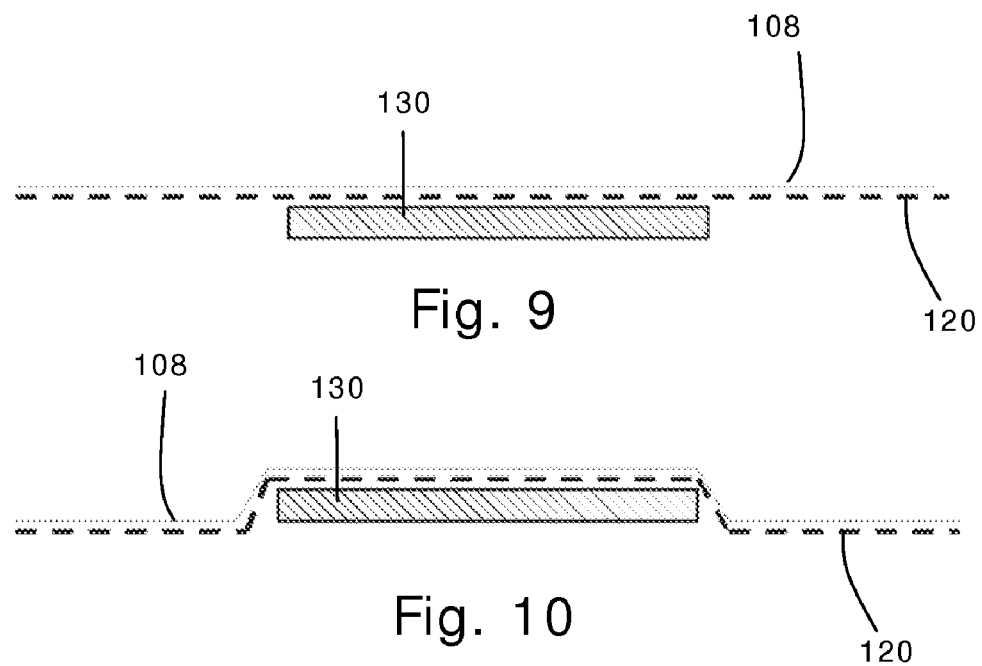
Fig. 9
Fig. 10

METHOD FOR MANUFACTURING A NET PATTERNED ADHESIVE LAYER

This is a national stage of PCT/EP08/056,909 filed Jun. 4, 2008 and published in English, which has a priority of Denmark no. PA 2007 00811 filed Jun. 4, 2007, hereby incorporated by reference.

FIELD OF THE INVENTION

This invention relates to medical adhesive tapes for use in adhering medical appliances, dressings, etc., to the skin. More specifically, the present invention is directed to a method of manufacturing a medical adhesive tape comprising a backing film, a net patterned adhesive layer, and a release liner.

BACKGROUND OF THE INVENTION

In medical fields, medical adhesive tapes such as surgical tapes, plasters (first-aid plasters), etc., are applied to adhere medical appliances, rolled bandages, wound dressings, transdermal absorbents, etc., to the skin.

The adhesive tape is composed of an adhesive which is coated on a backing layer. Such an adhesive tape should have adhesion suitable for firmly adhering the medical appliances or dressing materials to the skin and subsequently easily removing them from the skin. Furthermore, the tape should have high water vapour permeability to avoid skin damage because it is directly attached to the skin, in which high water vapour permeability can promote wound healing.

Conventionally, the adhesive tape has the pressure-sensitive adhesive (PSA) coated onto an entire surface of the backing layer. Thus, conventional tapes are disadvantageous in terms of low water vapour permeability, due to the coated adhesive per se, regardless of the water vapour permeability of the backing layer. That is, even though a backing layer having high water vapour permeability is used, the adhesive coated on the entire surface of the backing layer may prevent water vapour permeation, whereby the water vapour permeability of the tape is reduced.

The user of the adhesive tape may come into contact with water. Hence, water or liquid resistance is required to protect the wound or medical appliance.

Dot-shaped patterns of pressure sensitive adhesives (PSA) coated on backing film allow increased vapour permeability at the areas which are not coated. However water infiltration or leakage is possible via the interconnected uncoated areas or channels, which are defined between the non-interconnected dots of a dot-shaped adhesive pattern.

Specifically, dot-coated parts are discontinuously formed, that is, the coating parts are not interconnected, whereby water is infiltrated between the coating parts. Such infiltration of water leads to maceration of the skin, which is harmful to the wound.

U.S. Pat. No. 6,171,648 discloses a backing material with a partial self-adhesive coating.

A net shaped adhesive on an unperforated backing film is known. Such coating also has the advantages of the dot coatings, with the connected net of adhesive being able to form barrier against leakage. The permeability of the net coating is limited by the area without adhesive and the permeability of the backing film.

WO 2005/028581 discloses a medical adhesive tape, having high water vapour permeability and water resistance, characterized in that a pressure-sensitive adhesive is coated on a base sheet to form a net-shaped structure. As such, the net-shaped structure includes a continuous rectilinear form having square pores, a continuous curvilinear form having slanted square pores, a continuous form having circular pores, or combinations thereof. The adhesive tape includes surgical tape and plasters serving to adhere medical appliances, rolled bandages, wound dressings, transdermal absorbents, etc., to the skin, and can permit the passage of a gas through a plurality of non-coating parts to have high water vapour permeability, and simultaneously have water resistance and sufficient adhesion through a continuous net type coating part.

The adhesives used in the known methods of manufacturing are often solvent based. Furthermore, a drying or curing step usually follows the pattern formation.

Most of the known coating methods can only coat one uniform thickness at one time.

Often there is some waste from the coating process in the equipment for making the patterns.

Typically the release liner totally encapsulates the adhesive.

Typically the net shaped adhesive known from the prior art is uniform in pattern, size and shape.

According to most of the known methods, the pattern is formed first, thereafter cured or dried, and finally followed by laying on a release liner.

Often the known methods of making net coatings involve coating a flowable mass which is subsequently made form-stable, e.g. by gelation. The interval between the coating and form-stable stage allows the adhesive mass the opportunity to flow. Especially for less viscous materials such as materials having a viscosity below 1 Pa·s, this flow out will mean that more of the backing film is covered by the adhesive than is intended. As the adhesive free area of backing film is reduced, the permeability of the adhesive layer is also reduced.

The net pattern produced by known methods is often such that the base surface/area in contact with the backing film is larger than the top surface/area, at the opposite end of the base area, due to flow. This reduces the adhesive used for contact with skin, and increases the adhesive covering the backing film thereby helping to increase permeability.

EP 5 532 275 discloses a non re-enforced and non-adherent dressing hydrophilic gel. The gel is manufactured by applying an aqueous solution to a mould defining a pattern of interconnected grooves and subsequently drying the solution in the mould to form the dressing.

DE 29 00 319 discloses a punching apparatus for making coiled bands with adhesives.

EP 0 437 916 discloses a method for producing an air-permeable adhesive tape by forming a layer of a solution on a substrate, the solution comprising an adhesive in an organic solution; applying water drops on said layer and evaporation the organic solvent contained so as to form an adhesive that contain water drops and finally evaporating the water. However, it will be appreciated, that the size and distribution of the water droplets are difficult to control.

As use of organic solvents is associated with environmental and health problems, it is an object of a preferred embodiment, to provide a method in which the adhesive does not contain organic solvents.

US 2005/0228329 discloses polymer material which in order to be gelled must be cooled down from a heated state. It will be appreciated that such heating and subsequently cooling is time consuming and accordingly, it is an object of a preferred embodiment of the present invention to provide a less time consuming method/process.

Often a release liner is added afterwards when the adhesive gel is sufficiently cold, for handling purposes, e.g. rolling up.

The liner, due to pressure exerted from it, may affect the final surface shape of coating depending on how far into gelation the adhesive has reached at the point of application of liner onto the coated adhesive.

A dressing normally contains a central part comprising an absorbent core.

If the absorbent core is directly attached to the middle of the coated backing layer, the adhesive area between the absorbent core and adhesive layer is largely wasted as it is not used for adhering to the skin as intended. The adhesive, though formulated for good properties for skin contact, may not have the optimal properties for attaching the absorbent core. For attachment of the absorbent core, a cheaper or more effective adhesive or attachment method may be used.

An exposed absorbent core on a backing film requires good anchorage to the backing film, especially when wet and heavy due to being soaked with exudate. By good anchorage is meant that absorption of moisture does not cause the absorbent core and the backing film to delaminate.

An exposed absorbent core surface facing the wound side maximises the exudate absorption when in place. However, longer term placement (such as for a period longer than 3-5 days) on the wound may lead to growth of tissue of the healing wound onto the absorbent core surface or more difficult removal, which in turn irritates the wound.

To overcome the removal problem, contact layers of less adhering nature are known. These contact layers are often thin films or gel layers having perforations to expose the absorbent core.

EP 633758 discloses an absorbent wound dressing having a layer of hydrophobic silicone gel which is intended to lie against the wound surface when the dressing is worn. A layer of carrier material carries the gel layer and affords the requisite strength thereto. An absorbent body is placed on that side of the carrier material and gel layer which lie distal from the wound surface in use. The carrier material and the gel layer have mutually coinciding penetrating perforations at least within the region of the absorbent body. A fluid barrier layer is provided on that side of the dressing which lies distal from the wound surface in use.

Another function of the contact layer may be to support and hold the absorbent core in position.

There is a need to simplify and improve the processes of making net patterned adhesive layer and especially for making dressing construction with different patterns at different parts of the same net patterned adhesive layer. There is a need to maximize the contact area to skin but minimize the coverage of the backing film. There is also a need to reduce the flow out of the edges of such coated patterns

SUMMARY OF THE INVENTION

The present invention relates to a method for making a net patterned adhesive layer by a mould, and a wound dressing comprising a net patterned adhesive layer.

BRIEF DESCRIPTION OF THE FIGURES

FIG. 7 illustrates a sectional view of an embodiment wherein the thickness and density of the net pattern adhesive layer varies throughout the film, FIG. 8 illustrates a sectional view of another embodiment in which the thickness and density of the net pattern adhesive layer varies throughout the film, FIG. 9 illustrates a sectional view of yet another embodiment, and FIG. 10 illustrates a sectional view of an even further embodiment.

DETAILED DESCRIPTION OF THE INVENTION

Figure 1:
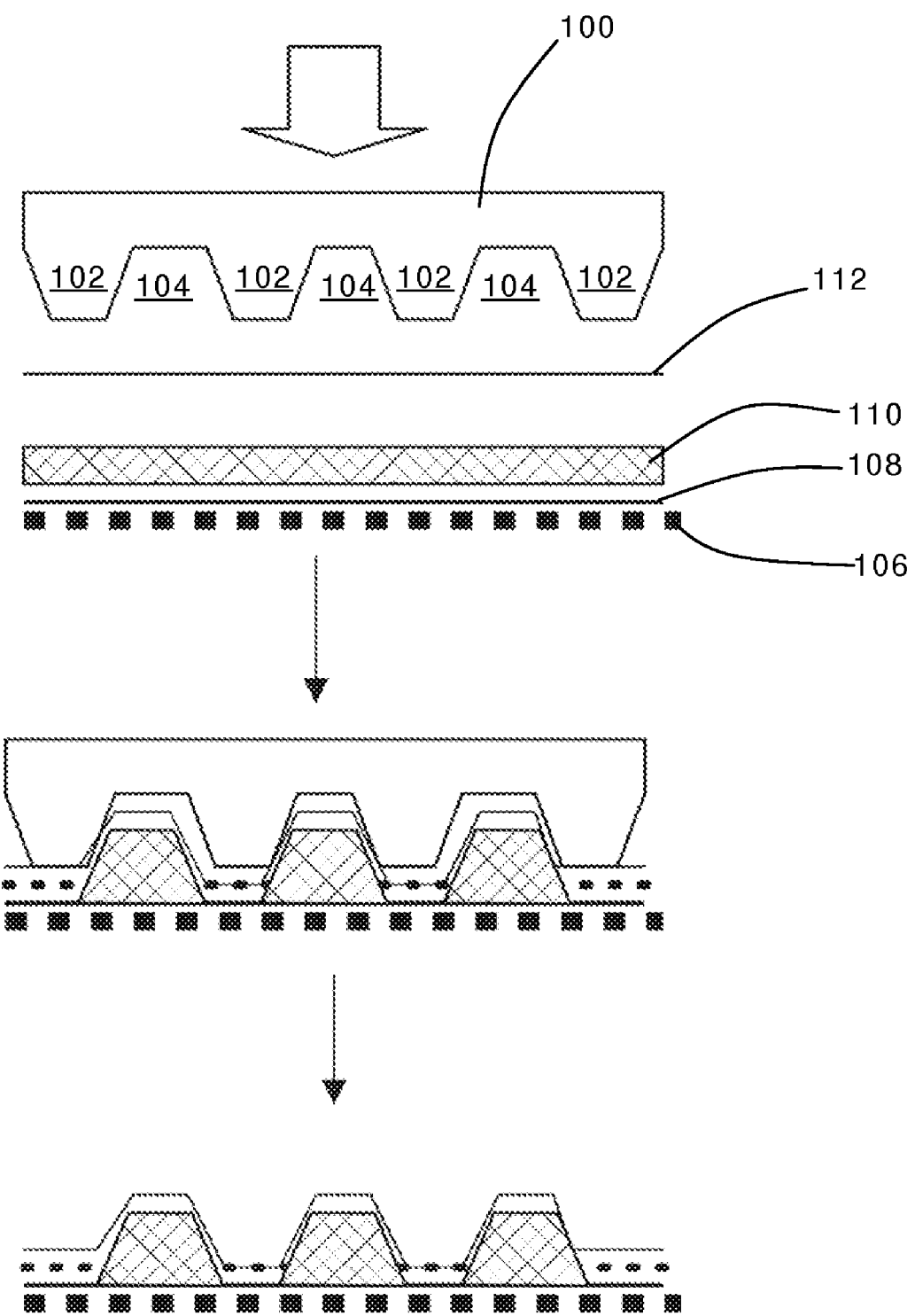
FIG. 1 illustrates a manufacturing method of the invention.

In a FIRST aspect the present invention relates to a method for making a net patterned adhesive layer for adhesion to the skin of a living being, which net patterned adhesive layer defines net with a predetermined pattern comprising adhesive zones spaced apart by spaces, the method comprising the steps of:

providing an adhesive in liquid form onto a support surface, forcing a moulding tool defining an inverse pattern which is inverse relative to the predetermined pattern onto an application area of the adhesive so as to define the predetermined pattern in the adhesive while the adhesive is in liquid form, allowing at least the outer surfaces of the adhesive in the application area to become form-stable by applying curing energy to the application area, at least a part of the curing energy being applied by or in the area of the moulding tool; and removing the moulding tool from the application area.

The current invention details a one step process of making a patterned adhesive layer, characterised in that the pattern of adhesive is a connected layer, and flow out of the adhesive at the base between the adhesive and backing film is minimised.

In the context of the present invention the term "curing energy" shall be understood as any energy source suitable for curing the adhesive. Examples are thermal energy (heat), UV-radiation, IR-radiation or microwaves.

In one embodiment, the temperature of the adhesive when applied to the supporting surface is below 60 degrees Celsius, such as below 40 degrees Celsius, such as below 30 degrees Celsius, such as below 25 degrees Celsius. In another embodiment, the temperature of the adhesive when applied to the supporting surface is at room temperature i.e. in the range of 18-25 degrees Celsius.

In one embodiment, the area inside at least a part of the spaces defined between the adhesive zones is substantially devoid of adhesive material.

In one embodiment, the area inside at least a part of the spaces comprises of a thin layer of adhesive the thickness of which is substantially thinner than the thickness of neighbouring adhesive zones.

In one embodiment, the area inside at least a part of the spaces comprises of a thin layer of adhesive the thickness of which is 0 to 10% of the thickness of neighbouring adhesive zones of the net.

In one embodiment the method comprises the step of providing a release liner on the adhesive prior to the step of forcing the moulding tool into the adhesive. The effect is that subsequent application of a release liner prior to rolling up the release liner for storage or handling may be eliminated.

In one embodiment, the moulding tool is cylindrical/drum-shaped, and the supporting surface is arranged to convey the liquid adhesive from an application area to a moulding area in which the moulding tool engages the adhesive. Moreover, the step of providing the adhesive and the step of forcing the moulding tool into the adhesive may be performed concurrently.

The backing film may be vapour permeable but unperforated.

The shape and dimensions of the net patterned adhesive layer may be uniform, or different at different areas of the film, e.g. may be larger areas without adhesive in the middle, lower thickness in the centre and higher thickness at the sides.

In one embodiment, the net pattern in two different areas relatively is not uniform in terms of at least one of:
 the distance between adhesive zones,
 the thickness of the adhesive zones,
 the width of the adhesive zones,
 the density of the adhesive zones and
 the cross-sectional shape of the adhesive zones.

In another embodiment of the invention the net pattern adhesive layer is less dense in the middle than in a rim portion thereof.

In one embodiment the adhesive zones are thicker in the area of the rim than in the middle/central part of the net. In another embodiment, the adhesive zones are thicker in the middle/central part and thinner in the rim portion. By thickness is meant the distance between two outer most surfaces of the adhesive at a given position in a direction parallel to a normal of the support surface during moulding (i.e., in the direction upwards and downwards in FIG. 1).

In one embodiment, the support surface defines a backing film, and the width of at least one of the adhesive zones in a base area which is in contact with the backing film is smaller than or equal to the width of a top area, which is defined by an opposite side of the adhesive zone.

It will be appreciated, that provision of a net pattern adhesive layer with a top area which is thinner than the base area, maximizes the adhesive used for contacting the skin, and minimizes the adhesive covering the backing film thereby helping to increase permeability.

The use of different patterns at different parts of the same adhesive layer in a dressing construction can reduce some of the drawbacks with a uniform net patterned adhesive layer which are mentioned in the introduction of this application.

The adhesive layer may be a so called transfer coating in which the adhesive is provided between two release liners such that the coating is suitable for being transferred onto a surface of the final product while leaving one of the surfaces protected by one of the release liners.

In another embodiment, the backing film is a permanent film suitable as a backing material for the adhesive in a dressing. By permanent film is meant a film which is used in a final product e.g. a wound dressing this is contrary to a release liner of a transfer film/coating which is adapted to be removed prior to application of the adhesive to a surface of the final product. It will be appreciated that in the case of a permanent backing film which is provided on one surface of the adhesive, a release liner may be provided on the opposite surface of the adhesive. The release liner may be removed prior to application of the final product (including the permanent backing film and the adhesive).

The backing film may be pre-treated, chemically or by corona treatment etc, to improve anchoring properties. Examples are silicone and titanate adhesion promoters.

In one embodiment of the invention the thickness of the net adhesive pattern layer is between 25 to 2000 µm, preferably 50 to 1000 µm.

The net patterned adhesive layer may cover between 25 to 90% of the backing film, or the adhesive area may constitute 25 to 90% of the total coated and uncoated surface of the backing film.

The adhesive is in a liquid form during coating and becomes a form-stable mass upon coating. The adhesive may be a two-component system. Preferably, the adhesive contains no solvent. Preferred adhesives include PU, acrylic, silicone (e.g. Silbione RTgel 4512 (Rhodia), Dow Corning 7-9800), or polyethylene or polypropylene oxide based crosslinking types as described in patent WO2005/032401. The adhesive may be a hotmelt type, which initially is heated to flow and subsequently cooled to gel or crosslink. Instead of curing upon cooling, the adhesive may in some embodiments cure upon application of thermal energy.

The peel force of the one or both of the adhesives may be below 10 N/cm, such as below 8 N/cm, such as below 6 N/cm, such as below 2 N/cm. It is preferred that the peel force of the adhesive face is max. 4N/cm In one embodiment, the adhesive layer forms part of a wound dressing which also comprises an absorbent core for absorbing wound exudate. The absorbent core and/or the adhesive gel may contain active ingredients, such as ibuprofen, paracetamol, silver or other medically active ingredients adapted to kill pain or to improve the healing of a wound.

Initial viscosity is preferably 0.1 to 1000 Pa·s, more preferably 0.5 to 100 Pa·s, such as 0.5 to 50 Pa·s.

Gelation is between 0 and 60 min., more preferably between 0.5 and 30 min at 25 to 130° C., to allow good coating processing (i.e. within less than a few minutes) and shape forming.

During manufacture the adhesive material may reach a form-stable state without being fully reacted.

In the context of the present invention the term "Form-stable" means that the material retains its shape under normal conditions, i.e. in the temperature range 25 to 130° C.

Full reaction or gelation may occur at a subsequent step of post-curing at which curing energy such as thermal energy may be provided to accelerate full reaction.

The moulding tool is suitably made of an inert low surface energy material, e.g. PTFE, or coated with a low surface energy coating, e.g. PTFE or silicone.

In order to achieve the predetermined pattern of the adhesive, the moulding tool will comprise protrusions extending away from a base level of the moulding tool i.e. towards the backing film during the moulding process. It will be appreciated that the net pattern will be defined by said protrusions, as the protrusions during application of pressure to the moulding tool during moulding will force the adhesive into the spaces defined between the protrusions of the moulding tool. The applied pressure between the moulding tool and the backing film, as well as the low surface energy, should ensure that substantially all of the adhesive will be forced to the spaced defined between the protrusions of the moulding tool, leaving a discontinuous area within the individual pattern without substantially any adhesive.

However, the invention is not limited to making net pattern adhesive layers where the enclosed areas defined within the individual net pattern adhesive layers must be totally devoid of adhesive.

Another embodiment of the invention relates to a method for making a net pattern adhesive layer where the enclosed areas within the net pattern adhesive layers consist of a very thin layer of the same adhesive, with or without holes, or a combination thereof.

The invention according to the first aspect may also be described in the following manner:

Embodiment 1

A method for making a net patterned adhesive layer by a mould wherein the adhesive mass is a liquid which becomes form stable before the mould is removed, and the heating for rendering the liquid mass form stable is at least partially from the mould.

Embodiment 2

The method according to embodiment 1 wherein the area side the individual pattern is largely devoid of adhesive material.

Embodiment 3

The method according to embodiment 1 wherein the area inside the individual pattern comprises of a thin layer of adhesive.

Embodiment 4

The method according to embodiment 1 wherein the area inside the individual pattern comprises of a thin layer of adhesive which is 0 to 10% of the thickness of the net.

Embodiment 5

The method according to any of the embodiments 1-4 wherein the net pattern is made with a release liner in place in contact with the adhesive.

Embodiment 6

The method according to any of the embodiments 1-5 wherein the method is made in one step.

Embodiment 7

The method according to any of the embodiments 1-6 wherein the net pattern is not uniform.

Embodiment 8

The method according to any of the embodiments 1-7 wherein the net pattern is less dense in the middle.

Embodiment 9

The method according to any of the embodiments 1-8 wherein the net pattern is of different thickness, preferably with a thicker pattern near the edge and thinner near the centre of the pattern.

Embodiment 10

The method according to any of the embodiments 1-9 wherein the net pattern is such that the base area in contact with the backing film is equal to the top area, at the opposite end of the base area.

Embodiment 11

The method according to any of the embodiments 1-9 wherein the net pattern is such that the base area in contact with the backing film is smaller than the top area, at the opposite end of the base area.

In a SECOND aspect the present invention relates an adhesive layer with patterned adhesive wherein the patterned adhesive is made according to method according to the first aspect of the invention.

In a THIRD aspect the present invention relates to a wound dressing comprising a vapour permeable but liquid impermeable backing film with a net adhesive pattern layer made according to the method according to the first aspect of the invention, and an absorbent core defining one or more borders, wherein the net pattern adhesive layer extends beyond the borders of the absorbent core.

The invention according to the third aspect may also be described in the following manner:

Embodiment A

A wound dressing comprising a vapour permeable but liquid impermeable backing film with a net adhesive pattern, and an absorbent core wherein the net adhesive layer extends beyond the borders of the absorbent core.

Embodiment B

The wound dressing according to embodiment A wherein the net pattern of the net adhesive layer is not uniform.

Embodiment C

The wound dressing according to any of the embodiments A-B wherein the net pattern of the net adhesive layer is with variation in densities preferably less dense in the middle.

Embodiment D

The wound dressing according to any of the embodiments A-C wherein the net pattern of the net adhesive layer is with variation in thickness preferably with a thicker pattern near the edge and thinner near the centre of the pattern.

Embodiment E

The wound dressing according to any of the embodiments A-D wherein the net pattern is such that the base area in contact with the backing film is equal to the top area, at the opposite end of the base area.

Embodiment F

The wound dressing according to any of the embodiments A-E wherein the net pattern is such that the base area in contact with the backing film is smaller than the top area, at the opposite end of the base area.

It will be appreciated that the invention according to the second and third aspect may comprise any combination of features and elements of the invention according to the first aspect.

DETAILED DESCRIPTION OF THE FIGURES

The invention will now be described in further detail with reference to the figures.

A manufacturing method of the invention may have a set up as illustrated in FIG. 1.

FIG. 1 discloses three drawings: an upper drawing, a middle drawing and a lower drawing. The upper drawing discloses the situation prior to application of pressure to the moulding tool 100. The moulding tool 100 defines a plurality of protrusions 102 between which indentations 104 are defined. It will be appreciated that the spaces defined between the protrusions 102 correspond to the final shape of the net adhesive layer.

Below the moulding tool 100 is provided a plurality of layers. At the very bottom is provided a support surface 106 for supporting the layers during processing and against which the moulding tool is forced so as to shape the net pattern adhesive layer. Initially a backing film 108 is provided on the support surface 106 and a pressure sensitive adhesive (PSA) 110 in liquid form is poured, cast or rolled onto the backing film 108. Subsequently, a release liner 112 is provided on top of the PSA-layer 110.

Subsequently, the moulding tool 100 is forced towards the support surface i.e. downwards in the drawing as is shown in the middle drawing. During the process, the moulding tool 100 may apply curing energy such as thermal energy to the layers below for a predetermined period. When the PSA-layer has achieved a form-stable state, the moulding tool 100 is removed as is shown in the lower drawing.

The liquid adhesive which during application has a low viscosity i.e. below 100 Pa·s, may be applied by means of conventional methods such as by being poured out through a slit-shaped opening. Pumps and static mixers (not shown) may be provided for feeding the liquid out through the slit-shaped opening.

In some embodiments, the surface of the applied layer is smoothened prior to being subjected to the moulding tool. Smooth coating of the right thickness may be achieved by any known means, e.g. die slot, doctors knife. Alternatively, or as a supplement, the press may be used to ensure the right spread and coating thickness.

Figure 2:
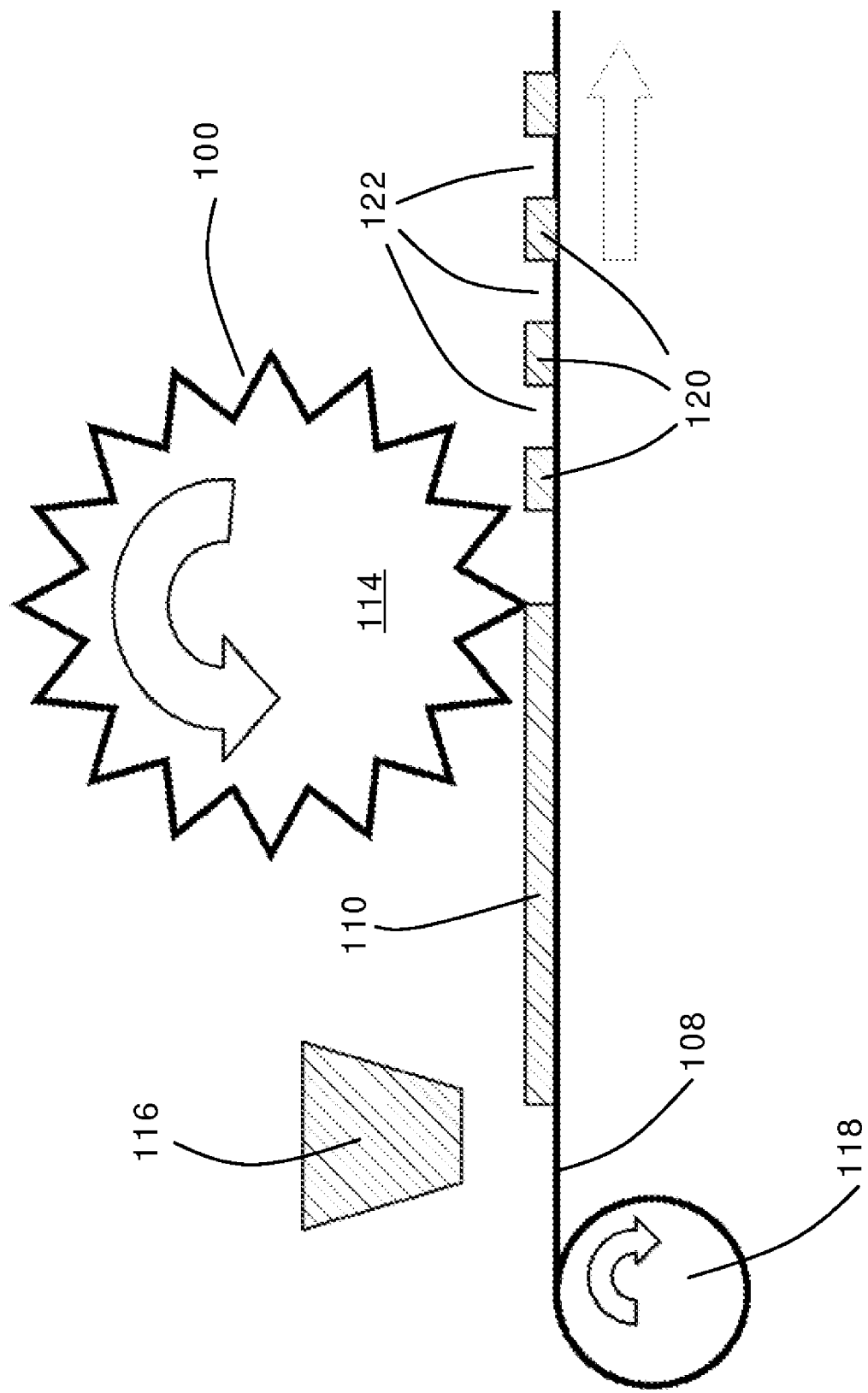
FIG. 2 illustrates a continuous manufacturing method of the invention.

The press may be in the form of a cylindrical drum with a patterned surface as is illustrated in FIG. 2.

The gelation, or increase in viscosity of the adhesive material to a form-stable state should be so fast enough to ensure that the material is prevent from flowing into uncoated areas, while at the same time allowing pre-gelled adhesive to move into the spaces defined by the indentations 104. Preferably the form-stable state is reached while the mould is in place.

The energy source for providing the curing energy may be any suitable source, e.g. microwaves, heat, UV-radiation, IR-radiation and may be applied from any direction, e.g. top or bottom. Preferably the heat is applied by means of the moulding tool.

Post-curing of the form-stable adhesive material is also a possibility.

A continuous manufacturing method of the present invention may have a set up as illustrated in FIG. 2 in which the moulding tool 100 is defined by a cylinder 114, the outer surface of which defines the inverse pattern, i.e. the pattern which is inverse the predetermined pattern the adhesive layer will have as a result of the method of the present invention.

In the embodiment of FIG. 2, the liquid adhesive 110 is poured onto the backing film 108 by means of an applicator 116 which may be a slit-shaped opening extending into the drawing, through which the liquid adhesive is feed.

As the backing film 108 is unrolled from a roll 118, the liquid adhesive is advanced towards the cylinder 114, which is pressed against the backing film 108 such that the predetermined pattern is formed in the adhesive layer 110. The predetermined layer defines adhesive zones 120 between which spaces 122 are defined. It will be appreciated that the rolling speed and the curing energy applied, e.g. by means of the moulding tool, should be chosen such that the adhesive has reached its form-stable state when it disengages from the moulding tool 100 of the cylinder 114.

Figure 3:
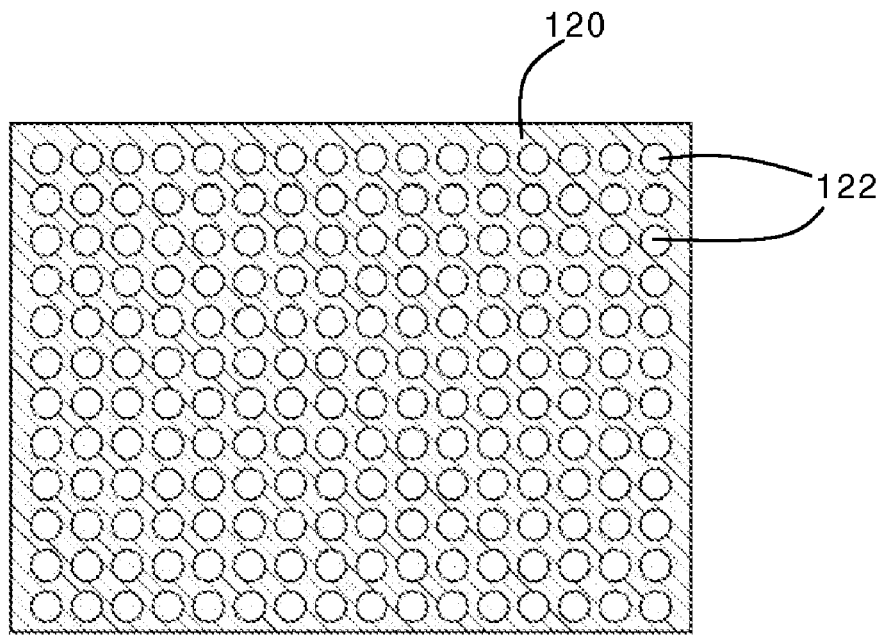
FIG. 3 illustrates a top view of an embodiment of the net patterned adhesive layer manufactured according to the invention.
Figure 4:
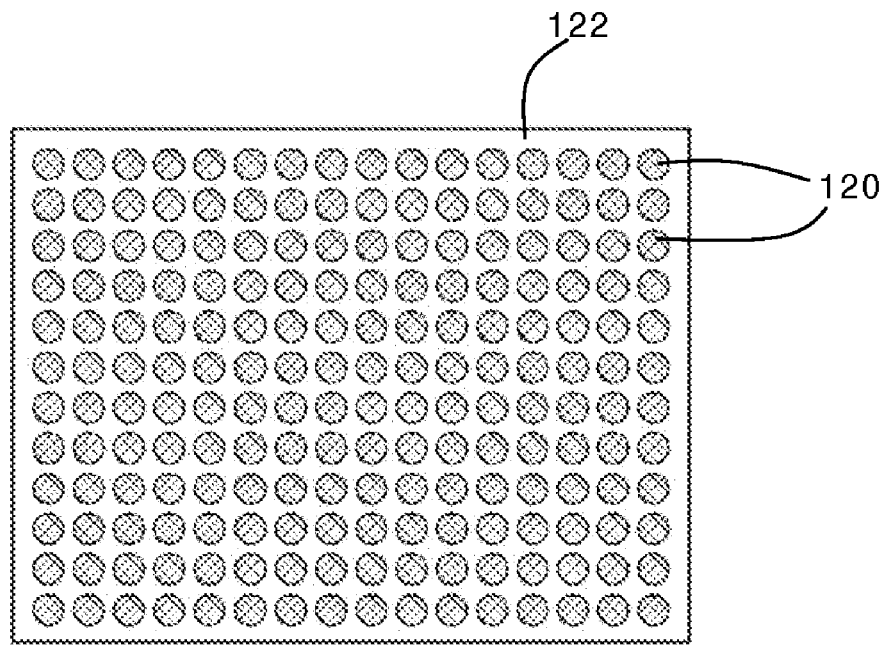
FIG. 4 illustrates a top view of another embodiment of the net patterned adhesive layer manufactured according to the invention.
Figure 5:
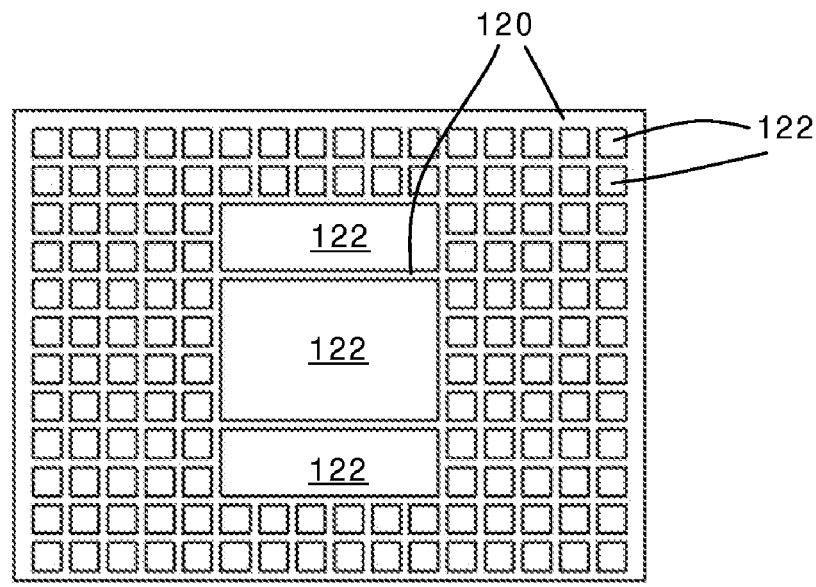
FIG. 5 illustrates a top view of yet another embodiment of the net patterned adhesive layer manufactured according to the invention.

FIGS. 3-5 illustrate top views of three alternative net pattern adhesive layers 100 manufactured according to the present invention.

The spaces 122 (the 'holes' or adhesive free surfaces) which may be of any shape or size, are distributed in any way desirable. The edges of the shapes 122 are characterised in that the adhesive edge is formed while the adhesive is a liquid and flowable. In some embodiments the outer form-stable surface of the adhesive layer may encapsulate non-form-stable material inside the adhesive zones of the net. Such encapsulated non-form-stable material may be post-cured so as to make it form-stable.

The thickness and density of the net pattern adhesive layers may vary throughout the film. FIGS. 7 and 8 illustrate the cross section of two alternatives with this variation.

In some embodiments of the invention the width of net pattern adhesive layer in the base area 124 contacting the backing film 108 is equal to the top area 126, which is provided at the opposite side of the adhesive zone 120 i.e. the surface facing away from the backing film 108.

In another embodiment (disclosed in FIG. 8), the width of net pattern adhesive layer in the base area 124 contacting the backing film 108 is smaller than width of the top area 126.

For example the middle or centre area of the net pattern adhesive layer may be a low thickness net pattern adhesive layer with large open uncoated areas, and the sides or edges of the layer may be a thicker and denser net pattern adhesive layer with less uncoated areas, or vice versa.

Inner area with large uncoated surface is better for welding of the absorbent core.

One advantage of the present invention is that the waste is reduced or even eliminated as no adhesive is cut away by a cutting tool. Instead all the adhesive is used to form the net pattern adhesive layer. In conventional methods, the pattern is achieved by removing the adhesive from predetermined areas of an adhesive film, e.g. by hole punching of a continuous layer of adhesive. Such conventional methods lead to scrap material, which increases costs and causes process problems due to possible residues in the holes.

Release liner can be part of the pattern making and is left on, without an extra step of putting on release liner for handling purposes afterwards.

The release liner suitably comprises a thermoplastic material with low Tg and melting point that can be moulded at the same process, e.g. LDPE, MDPE, HDPE. The temperature and duration of the moulding and gelation is chosen such that the release liner can deform permanently to the shape of the mould but not melted to reveal tears in the holes/perforations.

Release liner may be coated with a release coating, e.g. silicone.

The backing films may be organic or synthetic, woven or non woven materials. The backing films may be patterned or textured.

In one embodiment, a wound dressing 128 comprises a non-uniform net pattern adhesive layer as is described previously.

Figure 6:
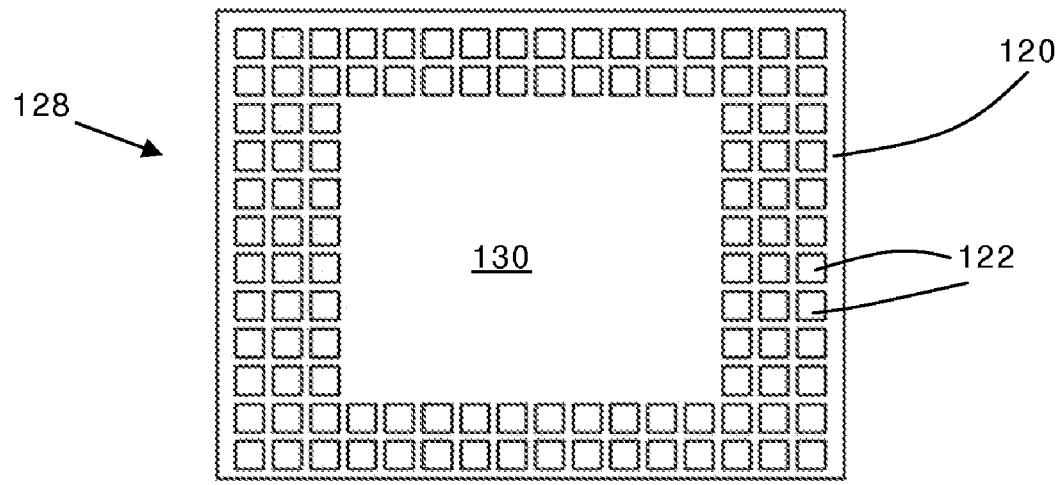
FIG. 6 illustrates a top view of an embodiment of a dressing utilising the advantages of having a non uniform net pattern adhesive layer.

The construction of a dressing 128 utilising the advantages of having a non uniform net pattern adhesive layer 110 is illustrated in FIG. 6.

The dressing 128 may be any shape, e.g. round or rectangular.

The backing layer has the net pattern adhesive layer on the wound facing side. The centre has an absorbent core, e.g. hydrophilic PU foam.

In one embodiment, a wound dressing comprises a vapour permeable but liquid impermeable backing film with a net pattern adhesive layer, and an absorbent core 130 wherein the net pattern adhesive layer extends beyond the borders of the absorbent core 130, see FIGS. 6, 9 and 10.

The dressing 128 is characterised in that the net pattern adhesive layer 110 extends beyond the edges of the absorbent core 130. The connected net pattern adhesive layer on this layer eliminates leakage problems due to channels when placed on an exudating wound.

In one embodiment, a wound dressing 128 comprises a net pattern adhesive layer in which with the density varies such that the density is lower in the centre thereof.

In another embodiment, a wound dressing 128 comprises a net pattern of the net adhesive layer which is with variation in thickness preferably with a thicker pattern near the edge and thinner near the centre of the pattern.

The absorbent core 130 may be attached to the backing layer by means of any known method, preferably by adhesive or welding. The attaching adhesive may be the same adhesive on the coated sheet. The welding or adhesive may cover entirely or only partially the surface of the backing facing layer FIG. 9 illustrates a sectional view taken along a line in the middle from one edge to the opposite edge of the dressing.

FIG. 10 illustrates a sectional view of another preferred construction where the layer 108 defines an indentation for accommodation of the absorbent core 130 whereby the surface facing the wound and the adhesive for attachment to the skin are provided at the same level.

The adhesive layer may be flat or is pushed back so that the wound facing surface is flat. The sides of the absorbent core 130 may also be sealed be adhesive or welding to the backing layer.

There may also be a contact layer on the absorbent core facing the wound, totally or partially over the core surface.

EXAMPLES

The invention will now described by way of the following examples which illustrate a method of pattern coating of an adhesive and the increase in permeability the pattern coating leads to, relative to conventional patterns.

Adhesives may be crosslinked polypropylene oxide adhesive (as described in patent WO2005/032401A2), silicone gel (e.g. Dow Corning 7-9800) or any other commonly used pressure sensitive adhesives.
Materials:

A polyurethane film (Bioflex 130, 25 µm from Scapa) was used as supporting film on which the adhesive was coated. Before coating, the surface of the film was treated with a primer (CF1-135 from Nusil) so as to improve adherence of the adhesive. The adhesive used was a polypropylene oxide adhesive (as described in patent WO2005/032401A2). A siliconised paper was used as release liner for the adhesive.
Method:

The surface of the polyurethane film was treated with the primer and subsequently fixated horizontally. The components [96.6% Allyl-terminated polyether (polypropylene oxide), viscosity 16 Pa·s., 3.3% Poly-alkyl hydrogen siloxane curing agent, 0.1% Pt-divinyl tetramethyl disiloxane] of the adhesive were mixed well together in a beaker. Subsequently, the adhesive was coated onto the polyurethane film with a knife-over technique, where the coating weight was controlled to secure a final thickness of approximately 200 µm.

Example I

In reference 2 (C2), the adhesive was subsequently covered with a release liner and cured in an oven for 30 minutes at 110° C.

Example II

In sample 1 (S1), the coated adhesive was covered with a release liner and, subsequently, pre-shaped by a pattern-die (illustrated in FIG. 3) which was pressed into the adhesive from the polyurethane film side. In the next step the die was heated to 110° C. to secure pre-curing in the pre-defined shape, so as to achieve a form-stable state. During pre-curing the moulding tool was pressed onto the adhesive for 10 seconds. Finally the adhesive was post-cured in an oven for 30 minutes at 110° C.

The pre-curing took place in a press, in which the pattern-die/moulding-tool was placed on the lower part of the press. Spacers were used to provide a total height over the die sufficiently high provide space for the release liner and polyurethane film. As a consequence the adhesive was pressed away from the upper most surfaces of the die, i.e. the aforementioned top areas.

Example III

In sample 2 (S2), the coated adhesive was covered with a release liner and subsequently pre-shaped by a pattern-die/moulding tool (corresponding to that of FIG. 6) which was pressed into the adhesive from the polyurethane film side.

Subsequently, the die was heated to 110° C. to secure pre-curing in the pre-defined shape, so as to achieve a form-stable state. During pre-curing, the moulding tool was pressed onto the adhesive for 10 seconds. Finally the adhesive was post-cured in an oven for 30 minutes at 110° C.

The moulding tool of the third example was shaped such that when pressed against the adhesive, any adhesive positioned below the central part of the moulding tool was forced away from said area so as to ensure an adhesive-free area (with a diameter of e.g. 60 mm) of the final adhesive product. It will be appreciated that in such a situation, the pressure should be so low that the risk of tearing holes in the polyurethane film is minimised. Thus even though no adhesive should ideally be present in the central area, a thin layer/film of adhesive may be present due to the chosen pressure.
Analysis:

When the samples of the above examples had cured, a sample for permeability analysis was punched, e.g. Ø45 mm.

The permeability was measured according to DS/EN 13726-2 Test methods for primary wound dressing—Part 2: Moisture Vapour Transmission Rate (MVTR) of permeable film dressings section 3.2. The following samples were analysed:

Reference 1 (C1)—Polyurethane (surface treated with primer)

Reference 2 (C2)—Polyurethane film coated with 200 µm adhesive

Sample 1 (S1)—Polyurethane film coated with 200 µm adhesive in pattern

Sample 2 (S2)—Polyurethane film coated with thin-pressed adhesive

Results:

The results in the below table clearly demonstrate that the pattern coatings provided an enhanced permeability compared to conventional coating of adhesives, e.g. C2

| Sample | Permeability [g/m2/24 h] |
|---|---|
| C1 | 1200 |
| C2 | 600 |
| S1 | 800 |
| S2 | 1200 |

The invention claimed is:

1. A method for making a net patterned adhesive layer for adhesion to the skin of a living being, which net patterned adhesive layer defines a net with a predetermined pattern including adhesive zones spaced apart by spaces, the method comprising the steps of:
   providing an adhesive in liquid form onto a support surface;
   forcing a moulding tool defining an inverse pattern which is inverse relative to the predetermined pattern on to an application area of the adhesive so as to define the predetermined pattern in the adhesive while the adhesive is in liquid form;
   allowing at least outer surfaces of the adhesive in the application area to become form-stable by applying curing energy to the application area, at least a part of the curing energy being applied by means of the moulding tool; and
   removing the moulding tool from the application area.

2. The method according to claim 1, wherein a temperature of the adhesive when applied to the support surface is below 60 degrees Celsius.

3. The method according to claim 1, wherein an area inside at least a part of the spaces is substantially devoid of adhesive material.

4. The method according to claim 1, wherein an area inside at least a part of the spaces includes a thin layer of adhesive having a thickness of which is substantially thinner than a thickness of neighbouring adhesive zones.

5. The method according to claim 1, wherein an area inside at least a part of the spaces includes a thin layer of adhesive having a thickness which is 0 to 10% of a thickness of neighbouring adhesive zones of the net.

6. The method according to claim 1, further comprising the step of providing a release liner on the adhesive prior to the step of forcing the moulding tool into the adhesive.

7. The method according to claim 1, wherein the moulding tool is drum shaped, and the support surface is arranged to convey the liquid adhesive from an application area to a moulding area in which the moulding tool engages the adhesive, and wherein the step of providing the adhesive and the step of forcing the moulding tool into the adhesive are performed concurrently.

8. The method according to claim 1, wherein the net pattern in two different areas, relatively, is not uniform in terms of at least one of: a distance between adhesive zones, a thickness of the adhesive zones, a width of the adhesive zones, a density of the adhesive zones and a cross-sectional shape of the adhesive zones.

9. The method according to claim 1, wherein the net pattern is less dense in a middle portion than in a rim portion thereof.

10. The method according to claim 1, wherein the adhesive zones are thicker in a rim area of the net than in a middle portion of the net.

11. The method according to claim 1, wherein the support surface defines a backing film, and wherein a width of at least one of the adhesive zones in a base area which is in contact with the backing film is substantially equal to a width of a top area, which is defined by an opposite side of the adhesive zone.

12. The method according to claim 1, wherein the support surface defines a backing film, and wherein a width of at least one of the adhesive zones in a base area which is in contact with the backing film is smaller than a width of a top area, which is defined by an opposite side of the adhesive zone.

13. An adhesive layer comprising patterned adhesive having a predetermined pattern, said patterned adhesive being made by providing an adhesive in liquid form onto a support surface, forcing a moulding tool defining an inverse pattern which is inverse relative to the predetermined pattern onto an application area of the adhesive so as to define the predetermined pattern in the adhesive while the adhesive is in liquid form, allowing at least outer surfaces of the adhesive in the application area to become form-stable by applying curing energy to the application area, at least a part of the curing energy being applied by means of the moulding tool, and removing the moulding tool from the application area.

14. A wound dressing comprising:
   a vapour permeable but liquid impermeable backing film with a net adhesive pattern layer having a predetermined pattern, said net adhesive pattern layer being made by providing an adhesive in liquid form onto a support surface, forcing a moulding tool defining an inverse pattern which is inverse relative to the predetermined pattern onto an application area of the adhesive so as to define the predetermined pattern in the adhesive while the adhesive is in liquid form, allowing at least outer surfaces of the adhesive in the application area to become form-stable by applying curing energy to the application area, at least a part of the curing energy being applied by means of the moulding tool, and removing the moulding tool from the application area; and
   an absorbent core defining one or more borders, wherein the net pattern adhesive layer extends beyond the borders of the absorbent core.

* * * * *